United States Patent [19]
Surburg et al.

[11] Patent Number: 6,034,268
[45] Date of Patent: Mar. 7, 2000

[54] 8-OCIMENYL ESTERS AND FRAGRANCES AND FLAVORS CONTAINING THE SAME

[75] Inventors: Horst Surburg; Horst Sommer; Stefan Lambrecht; Peter Wörner; Matthias Güntert, all of Holzminden; Günter Kindel, Höxter; Volkmar Koppe, Holzminden, all of Germany

[73] Assignee: Haarmann & Reimer GmbH, Holzminden, Germany

[21] Appl. No.: 09/186,267

[22] Filed: Nov. 4, 1998

[30] Foreign Application Priority Data

Nov. 5, 1997 [DE] Germany ............... 197 48 774

[51] Int. Cl.[7] .................. C07C 69/587; C07C 67/10; C07C 57/03; C07C 51/02
[52] U.S. Cl. .................. 560/261; 560/205; 560/213; 560/225; 560/237; 562/598; 562/599
[58] Field of Search ................. 560/205, 237, 560/213, 225, 261; 562/598, 599

[56] References Cited

U.S. PATENT DOCUMENTS

| 4,510,319 | 4/1985 | Willis et al. | 560/231 |
| 5,756,821 | 5/1998 | Dilk et al. | 560/129 |

FOREIGN PATENT DOCUMENTS

| 0 761 629 A1 | 3/1997 | Germany . |
| 63227546 | 9/1988 | Japan . |

OTHER PUBLICATIONS

S. Hedge, et al., "The Reaction Of Hypochlorous Acid With Olefins. A Convenient Synthesis Of Allylic Chlorides", Tetrahedron Letters, vol. 21, pp. 441–444 (1980).

M. Bulliard, et al., "Chloration Allylique D'Olefines De Type Isoprenique A L'Aide Du Chlorure De Sulfuryle", Tetrahedron Letters, vol. 30, No. 42, pp. 5767–5770 (1989).

Beilstein CrossFire, 1 page Dunlop, R. W. et al. AJCHAS, Aust. J. Chem., EN 32, (1979), 2735–2739.

European Search Report dated Jan. 2, 1999.

S. Arctander, "Perfume and Flavour Chemicals", 2388: Ocimene; 2389: Ocimenol; and 2390: cis–Ocimenyl Acetate, Montclair, N.J. (1969).

Dunlop, R.W., et al., "A New Polyhalogenated Monoterpene from the Red Alga Plocamium angustum" *Aust. J. Chem.*, vol. 32, pp. 2735–2739 (1979).

*Primary Examiner*—Rosalynd Keys
*Attorney, Agent, or Firm*—Brinks Hofer Gilson & Lione

[57] ABSTRACT

Compounds of the formula

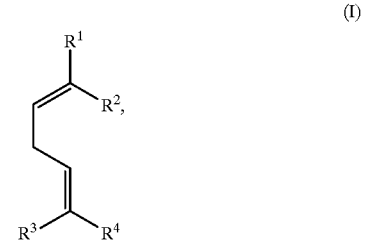

(I)

in which one of the radicals $R^1$ and $R^2$ is methyl and the other is vinyl and one of the radicals $R^3$ and $R^4$ is methyl and the other is

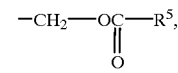

in which $R^5$ is hydrogen, alkyl or alkenyl, in particular $C_1$–$C_6$-alkyl or $C_2$–$C_6$-alkenyl, are particularly suitable as fragrances and flavors.

11 Claims, No Drawings

8-OCIMENYL ESTERS AND FRAGRANCES AND FLAVORS CONTAINING THE SAME

BACKGROUND OF THE INVENTION

1. Field of the Invention

The invention relates to 8-ocimenyl esters, to processes for their preparation and to their use as fragrances and flavours.

2. Discussion of the Background

In the perfume and flavour industry, there continues to be an increased demand for substances which can be used in perfume and flavour compositions as complete or partial replacements for those natural substances which, because of their laborious method of isolation, are expensive and available in limited amounts and, moreover, whose properties are subject to considerable quality fluctuations which arise by virtue of these substances being natural.

Particularly interesting substances are those which have not only excellent organoleptic properties (i.e. properties perceptible only by the senses), but with which it is also possible to attain, because of their strength and extendability, notable effects with the smallest of amounts.

The novel compounds, the esters of the 8-ocimenols, are potential perfume and flavour components to which these properties are particularly applicable.

Cis- and trans-ocimene (compounds of the formula 1 and 2 respectively) are terpene hydrocarbons which are very widespread in nature. Cis-ocimene is available commercially by pyrolysis of alpha-pinene. Ocimene derivatives which have achieved importance are essentially only 6,7-dihydroocimen-7-ol ("ocimenol") of the formula 3 and its acetate, 6,7-dihydroocimen-7-yl acetate ("ocimenyl acetate") of the formula 4 (see S. Arctander; Perfume and Flavor Chemicals, published privately, Montclair, N.J., 1969, Monograph 2389 and 2390.).

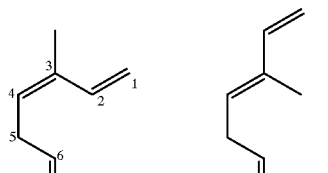

1
cis-ocimene 2
trans-ocimene

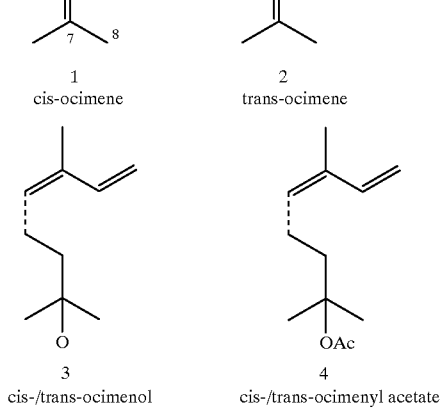

3
cis-/trans-ocimenol 4
cis-/trans-ocimenyl acetate

The ocimenol of the formula 3 has a fresh-camphoraceous lime-like odor with a sweet-floral base note; the ocimenyl acetate of the formula 4 has a sweet-fresh, herbal, citrus-like note.

DESCRIPTION OF THE INVENTION

We have now found compounds of the formula

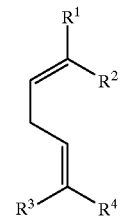

(I)

in which one of the two radicals $R^1$ and $R^2$ is methyl and the other is vinyl and one of the two radicals $R^3$ and $R^4$ is methyl and the other is

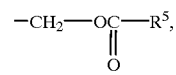

in which $R^5$ is hydrogen, alkyl or alkenyl, in particular $C_1$–$C_6$-alkyl or $C_2$–$C_6$-alkenyl.

Particular preference is given to those compounds of the formula (I) in which $R^5$ is hydrogen, methyl, ethyl, n-propyl, isopropyl, n-butyl, sec-butyl, isobutyl, tert-butyl or 2-butenyl, in particular methyl.

Very particular preference is given to compounds of the formula (I) which conform to the formulae (Ia)–(Id):

(Ia)

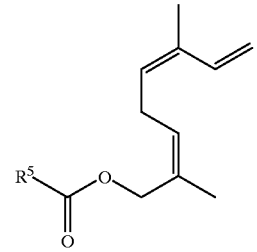

(Ib)

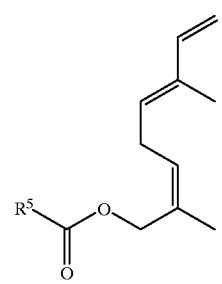

-continued

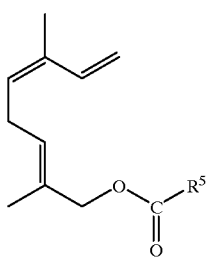
(Ic)

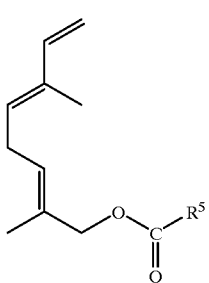
(Id)

in which $R^5$ is as defined above.

Of these formulae (Ia)–(Id), preference is given to the compound (Ib), in particular where $R^5$=methyl.

The novel compounds surprisingly produce a completely different type of odoriferous impression compared with the known compounds 3 and 4.

The invention also relates to a process for the preparation of compounds of the formula (I), characterized in that compounds of the formula

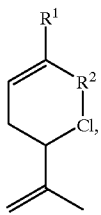
(II)

in which $R^1$ and $R^2$ are as defined above, are reacted with the salt, in particular an alkali metal salt, such as an Na or K salt, of an aliphatic carboxylic acid, in particular of a $C_2$–$C_7$-carboxylic acid.

The novel process is preferably carried out in an organic solvent, in particular in a dipolar, aprotic solvent. Suitable examples thereof are dimethylformamide, dimethyl sulphoxide, N-methylpyrrolidone, diethyl glycol dimethyl ether and mixtures thereof. The reaction is preferably carried out at a temperature of from 50 to 150° C., in particular at from 90 to 1 20° C., if necessary under pressure.

The novel process, which uses the compounds of the formula (II) as starting materials, is preferably carried out in the presence of an alkali metal iodide or elemental iodine, in particular in the presence of NaI, this additive preferably being used in catalytic amounts, in particular in an amount of from 0.01 to 10% by weight, based on II.

In the novel process, the compound of the formula (II) can be used as the E- or Z-isomer or as any E/Z mixture.

If the E/Z mixture of the formula (II), i.e. a mixture of a compound (II) in which $R^1$ is methyl and $R^2$ is vinyl and a compound (II) in which $R^1$ is vinyl and $R^2$ is methyl, is used, then a mixture comprising the compounds of the formulae (Ia)–(Id) is obtained.

In a particularly preferred process, sodium acetate is used as the salt of an aliphatic carboxylic acid.

The invention further relates to a process for the preparation of compounds of the formula (II), in particular those of the formulae (IIa) and (IIb)

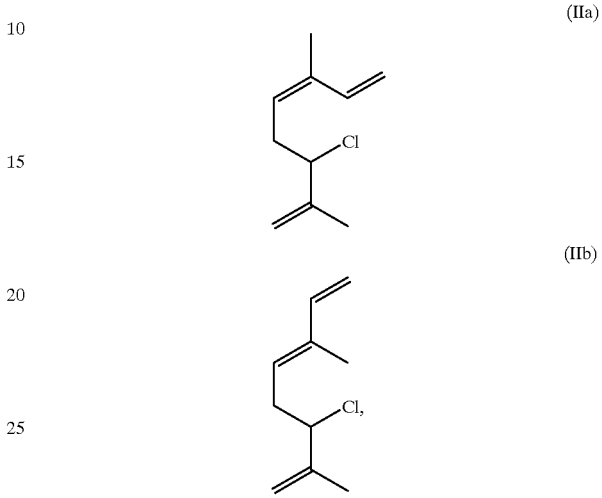

characterized in that ocimene of the formula

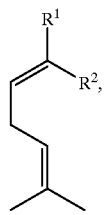
(III)

in which $R^1$ and $R^2$ are as defined above,
is reacted with hypochlorous acid or sulphuryl chloride ($SO_2Cl_2$).

For the reactions with hypochlorous acid, the latter is usually obtained in situ from salts of the hypochlorous acid by acidification. For the preparation of II, it has proven advantageous to liberate hypochlorous acid from sodium hypochlorite solution by acidification with acetic acid. The reaction with ocimene then proceeds in a two-phase system, the presence of a solvent is not necessary. The reaction temperature can be between 0 and 50° C., preferably between 10 and 20° C.

The chlorination using sulphuryl chloride is preferably carried out in the presence of a base, preferably in the presence of an alkali metal carbonate, such as sodium carbonate or potassium carbonate, which is used in particular in excess, based on sulphuryl chloride. Possible solvents which may be used are compounds which are inert towards sulphuryl chloride, such as hydrocarbons, preferably n-hexane or n-heptane, or halo-genated hydrocarbons, preferably dichloromethane or carbon tetrachloride, or ethers, preferably methyl tert-butyl ether. The reaction temperature is in particular from 0 to 50° C., preferably from 20 to 30° C.

The ocimene can in this connection be used as cis-ocimene of the formula (I), as trans-ocimene of the formula (2) or as a cis/trans mixture.

An ocimene cis/trans mixture is preferred, in which case a content of from 50 to 90% by weight of trans-isomers and from 50 to 10% by weight of cis-isomers is preferred, from which it is possible to prepare an E/Z mixture of the compound of the formula (II), and from this in turn a mixture of isomeric 8-ocimenyl esters of the formulae (Ia)–(Id).

The invention further relates to a process for the preparation of compounds of the formula (I) which is characterized in that compounds of the formula

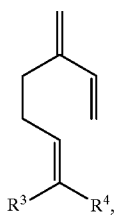

(IV)

in which $R^3$ and $R^4$ are as defined above,
are isomerized in the presence of a rhodium catalyst to give compounds of the formula (I).

The rhodium catalyst is preferably used in an amount of from 0.1 to 5% by weight, based on IV. The reaction can be carried out using an organic solvent, although it is preferably carried out without a solvent. The isomerization is preferably carried out at a temperature of from 100 to 200° C., in particular from 140 to 170° C.

Compounds of the formula (IV) can be prepared, for example, by reacting a compound of the formula

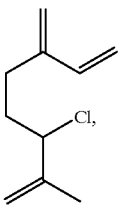

(V)

with a salt, in particular an alkali metal salt, such as an Na or K salt, of an aliphatic carboxylic acid, in particular of a $C_2$–$C_7$-carboxylic acid.

The preferred variants of this procedure are the same as those given for the process for the preparation of the compound I from II described above.

The compound of the formula (V) can in turn be prepared by reacting myrcene, a compound of the formula

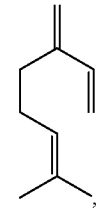

(VI)

with hypochlorous acid, the process conditions already given for the preparation of the compound II described above applying here as well.

If isomeric mixtures of two or more compounds of the formula (I) are produced, in particular the compounds (Ia)–(Id), they can be separated, for example, by preparative gas chromatography or else be used directly as mixtures.

The pure compound of the formula (Ib) where $R^5$=methyl has been found to be the main component responsible for the strong galbanum, pineapple-like odor of the isomeric mixture. The other isomers of the formulae (Ia), (Ic) and (Id) where in each case $R^5$=methyl had varying degrees of a fruity odor. The odors of these isomers are particularly suitable for rounding off and enhancing the pineapple-like freshness of isomer (Ib).

The invention thus also relates to mixtures comprising at least one compound of the formula (Ib) and at least one of the compounds (Ia), (Ic) and (Id), $R^5$ being as defined above.

The novel compounds of the formula (I) can also be converted into one another, for example by hydrolysis of an ester of the formula (I) and esterification to give another compound of the formula (I).

The mixture of the isomeric 8-ocimenyl acetates obtained by the novel process, for example, is characterized by a typical, strong green-fruity, pineapple-like odor and taste, whose tonality is very strongly reminiscent of essential galbanum oil. This galbanum oil is obtained by steam distillation from the resin of roots of a variety of Ferula species which grow wild in the Near East, mainly Iran. Because of the laborius method of obtaining the resin, galbanum oil is one of the more costly natural raw materials which are used in the perfume and flavour industry.

The other low molecular weight esters of the 8-ocimenols also have notable sensory properties:

The novel compounds of the formula (I) and their isomeric mixtures are especially suitable, because of their excellent organoleptic character, as fragrances and flavors for use in perfume oils and flavor compositions. It is particularly surprising that they impart a notable natural freshness and radiance to the composition in question without their own character being too dominant in the composition, i.e. the green-fruity note being too much in the foreground. On the whole, then, the overall sensory impression of fragrance and flavour compositions is upgraded and enhanced to a considerable extent as a result of the novel compounds being added.

The novel compounds of the formula (I) can be very easily combined with other fragrances and flavors in different varying mixing ratios to give new types of perfume and flavour compositions. In perfume compositions, the amount of compounds of the formula (I) used is from 0.01 to 10% by weight, preferably from 0.05 to 1%, based on the overall composition.

Such perfume compositions can be used not only in alcoholic solution as fine perfume, but also for perfuming cosmetics, for example creams, lotions, aerosols, toilet soaps, etc., household products such as cleaners and laundry detergents, fabric softeners, disinfectants and textile treatment agents and other industrial products, the amount of the perfume composition preferably being from 0.1 to 40% by weight, in particular from 0.5 to 20% by weight, based on the total product.

In flavor compositions, the amount of the novel compound of the formula (I) used is preferably from 0.01 to 10% by weight, in particular from 0.1 to 5% by weight, based on the overall composition. Such flavour compositions can be used in the entire foodstuffs and luxury products sectoir, as well as in products for oral hygiene. They are particularly suitable for flavoring fatty products, bakery products, yogurt, ice cream, sweets, chewing gum, alcoholic and non-alcoholic beverages, tobacco, toothpaste and mouthwashes. These types of flavor compositions are preferably added in amounts of from 0.0005 to 2% by weight, in particular from 0.01 to 1% by weight, based on the finished foodstuff or luxury product.

The percentages in the examples below are in each case by weight.

EXAMPLES

Example 1

Preparation of 8-ocimenyl acetate from ocimene a) Preparation of (Z)- and (E)-6-chloro-3,7-dimethyl-1,3,7-octatriene by aa) reaction of hypochlorous acid with ocimene 220 g of approximately 7% sodium hypochlorite solution were added drop-wise with vigorous stirring to a mixture, cooled to 10° C., of 27.2 g of ocimene (E/Z ratio about 1:1) and 32 g of acetic acid over the course of 1 h. A reaction temperature of between 10 and 15° C. was maintained throughout. After the reaction mixture had been stirred for a further 2 h at 10–15° C., the reaction was completed by stirring the mixture with 200 ml of diethyl ether. The organic phase was separated off, washed with water, bisulphite solution and bicarbonate solution and evaporated at room temperature under reduced pressure to give about 40 g of residue, which was reacted without further purification.

ab) reaction of sulphuryl chloride with ocimene 108.8 g (0.80 mol) of ocimene (E/Z ratio about 2:1) and 85 g of soda are mixed with 500 ml of methyl tert-butyl ether. At from 20 to 27° C., 100 g (0.74 mol) of sulphuryl chloride are metered in with cooling over the course of from 1 to 1.5 h. The reaction is slightly exothermic. The mixture is then stirred for from 2 to 3 h, during which slight evolution of gas can be observed. For work-up, the solid is filtered off with suction and the filtrate is washed with 5% strength sodium hydroxide solution and water, dried over sodium sulphate and evaporated. Distillation of the residue produces, at a head temperature of from 46 to 72° C. and 1 mbar of pressure, an approximately 90 g fraction having a combined content of isomeric chloroocimenes of about 75%.

b) The residue obtained in aa) was added to a mixture, heated to 100° C., of 82 g of sodium acetate, 3 g of sodium iodide and 300 ml of dimethylformamide. After the reaction mixture had been stirred at 100° C. for 2 h, it was cooled, diluted with 500 ml of water and extracted with 300 ml of hexane. The hexane extract was washed with water and dried, and the hexane was stripped off under reduced pressure. The residue which remained was about 30 g of crude product, which was filtered through a short silica gel column with a solvent mixture of 95% of hexane and 5% of ethyl acetate to remove darkly coloured polymeric products. The solvent was stripped off to leave about 15 g of product which had only a slight coloration and which was further purified by column chromatography on 400 g of silica gel with 95% of hexane/5% of ethyl acetate. About 10 g of an isomeric mixture were obtained, which was characterized by a penetrating, fruity pineapple-like odour reminiscent of galbanum oil.

Separation of the isomeric mixture by preparative gas chromatography and subsequent spectroscopic analysis showed that the isomeric mixture consisted of about 30–35% of (Z3,Z6)-8-ocimenyl acetate, 30–35% of (E3,Z6)-8-ocimenyl acetate, 10–15% of (Z3,E6)-8-ocimenyl acetate and 10–15% of (E3,E6)-8-oxymenyl acetate.

Characterization of compounds of the formulae (Ia)–(Id) where $R^5$=methyl (Ia) (Z3,Z6)-8-Ocimenyl acetate: slightly fresh-green, fruity.
(Ib) (E3,Z6)-8-Ocimenyl acetate: strongly galbanum-like, green, fruity, pineapple.
(Ic) (Z3,E6)-8-Ocimenyl acetate: green, fruity, pineapple.
(Id) (E3,E6)-8-Ocimenyl acetate: fresh, green, ester-like, floral.

The respective isomers were assigned to the individual structures on the basis of a comparison of 13-C-NMR spectra (see Table 1).

TABLE 1

Characteristic $^{13}$C-NMR signals of 8-ocimenyl acetate isomers

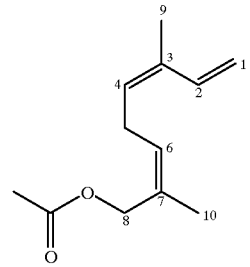

| | Compound No. | | | |
|---|---|---|---|---|
| C atom No. | (Ia) | (Ib) | (Ic) | (Id) [ppm] |
| 2 | 132.90 | 141.02 | 132.93 | 141.06 |
| 8 | 62.77 | 63.18 | 68.04 | 69.48 |
| 9 | 19.46 | 11.64 | 19.49 | 11.14 |
| 10 | 21.39 | 21.37 | 13.74 | 13.37 | c) The chlorocimene obtained in Example 1 ab) is reacted as in the process described under Example 1 b). After work-up, 90 g of crude product are obtained, which, after distillation over a short column at a reduced pressure of 4 mbar and a head temperature of 95° C., produce 50 g of an 8-ocimenyl acetate mixture, which, according to GC (gas chromatographic analysis), consists of 25% of the (Z3,Z6)-isomer, 40% of the (E3,Z6)-isomer, 10% of the (Z3,E6)-isomer and 15% of the (E3,Z6)-isomer.

Example 2

Preparation of 8-ocimenyl Acetate from Myrcene:

a) 27.2 g of myrcene were chlorinated as described in Example 1a.

b) The resulting crude product was reacted and worked up as described in Example 1b to give about 15 g of 8-myrcenyl acetate which, according to gas chromatographic analysis, comprised 60% of the (Z)-isomer and 30% of the (E)-isomer.

c) 0.01 g of BHT and 0.25 g of bis(octadienyl)rhodium I chloride were added to 10 g of the mixture obtained under b) and the whole mixture was heated at 160° C. under a nitrogen atmosphere for 1 h. Work-up of the reaction mixture by short-path distillation (bulb-to-bulb) gave about 6 g of 8-oxymenyl acetate comprising about 20% of (Z3,Z6)-8-ocimenyl acetate, 40% of (E3,Z6)-8-ocimenyl acetate, 10% of (Z3,E6)-8-ocimenyl acetate and 20% of (E3,E6)-8-ocimenyl acetate.

Thus, the 2:1 mixture of (Z)- and (E)-8-myrcenyl acetate produces the 8-oxymenyl acetates in the order given in a ratio of 2:4:1:2.

Example 3

Preparation of Other 8-ocimenyl Esters.

a) Hydrolysis of 8-ocimenyl acetate: 25 g of an 8-ocimenyl acetate mixture obtained in Example 1b were added to a solution of 36.5 g of potassium hydroxide in 265 ml of methanol. The reaction mixture was left to stand at room temperature for 24 h. After this time, the methanol was stripped off under reduced pressure and the residue was taken up in water and extracted using hexane. The extract was evaporated to give 18.8 g of residue, which was used without further purification for the esterification reactions described below.

b) 8-Ocimenyl formate:

1.9 g of formic acid were added to 3.2 g of acetic anhydride with cooling. The mixture is briefly heated to 50° C. then cooled to 5° C., and 3.2 g of the crude product obtained under 3a are added. After the mixture had been left to stand for 24 h, it was diluted with diethyl ether and washed with water and bi-carbonate solution. The organic phase was evaporated to leave 3.5 g of 8-ocimenyl formate, which had the same isomeric composition as the starting material. In order to determine the sensory properties, the individual isomers were isolated in pure form by preparative gas chromatography.

Formates:

(Z3,Z6)-8-Ocimenyl formate: fresh, fatty, green, fruity.
(E3,Z6)-8-Ocimenyl formate: fruity, fresh, sparkling, pineapple, galbanum.
(Z3,E6)-8-Ocimenyl formate: green, fruity, galbanum-like.
(E3,E6)-8-Ocimenyl formate: fatty, green, fruity, tropical fruit.

| Mass spectra of the 8-ocimenyl formates | | | | | | | |
|---|---|---|---|---|---|---|---|
| (3Z,6Z) m/z | Intens. (%) | (3E,6Z) m/z | Intens. (%) | (3Z,6E) m/z | Intens. (%) | (3E,6E) m/z | (%) |
| 119 | 100 | 119 | 100 | 119 | 100 | 119 | 100 |
| 91 | 67 | 91 | 56 | 93 | 98 | 91 | 72 |
| 93 | 48 | 134 | 47 | 91 | 90 | 93 | 63 |
| 79 | 47 | 79 | 39 | 79 | 71 | 79 | 62 |
| 134 | 43 | 77 | 31 | 92 | 65 | 77 | 45 |
| 77 | 39 | 93 | 31 | 77 | 55 | 41 | 40 |
| 41 | 37 | 41 | 31 | 41 | 47 | 134 | 39 |
| 39 | 31 | 39 | 27 | 134 | 44 | 39 | 32 |
| 92 | 30 | 55 | 24 | 105 | 42 | 105 | 32 |
| 105 | 28 | 105 | 23 | 39 | 39 | 80 | 31 |
| 180 (M+) | 0.12 | 180 (M+) | 0.04 | 180 (M+) | 0.17 | 180 (M+) | 1 | c) 8-Ocimenyl propionate:

3.2 g of the crude product obtained under 3a and 2.5 g of pyridine were dissolved in 25 ml of diethyl ether, and 2.3 g of propionyl chloride were added at 0° C. After the mixture had been left to stand for 24 h, it was diluted with water and washed with dilute hydrochloric acid, water and bicarbonate solution. The organic phase was evaporated to leave 4.2 g of 8-ocimenyl propionate, which had the same isomeric composition as the starting material. In order to determine the sensory properties, the individual isomers were isolated in pure form by preparative gas chromatography.

Popionates:

(Z3,Z6)-8-Ocimenyl propionate: fruity, sweet, fatty, green.
(Z3,Z6)-8-Ocimenyl propionate: green, fatty, galbanum.
(Z3,E6)-8-Ocimenyl propionate: fruity, sweet
(Z3,E6)-8-Ocimenyl propionate: fresh, fruity, sweet, floral.

| Mass spectra of the 8-ocimenyl propionates | | | | | | | |
|---|---|---|---|---|---|---|---|
| (3Z,6Z) m/z | Intens. (%) | (3E,6Z) m/z | Intens. (%) | (3Z,6E) m/z | Intens. (%) | (3E,6E) m/z | (%) |
| 119 | 100 | 119 | 100 | 57 | 100 | 119 | 100 |
| 57 | 55 | 57 | 43 | 119 | 97 | 57 | 83 |
| 91 | 39 | 134 | 35 | 91 | 48 | 91 | 39 |
| 29 | 34 | 91 | 34 | 92 | 45 | 134 | 38 |
| 134 | 33 | 29 | 29 | 29 | 44 | 29 | 38 |
| 92 | 24 | 79 | 19 | 93 | 43 | 79 | 30 |
| 93 | 23 | 105 | 18 | 134 | 38 | 93 | 29 |
| 79 | 22 | 93 | 17 | 79 | 33 | 92 | 24 |
| 105 | 22 | 92 | 16 | 105 | 31 | 105 | 22 |
| 77 | 19 | 41 | 16 | 77 | 26 | 77 | 21 |
| 208 (M+) | 0.12 | 208 (M+) | 0.08 | 208 (M+) | 0.22 | 208 (M+) | 0.12 | d) 8-Ocimenyl crotonate:

3.2 g of the crude product obtained under 3a and 2.5 g of pyridine were dissolved in 25 ml of diethyl ether, and 2.6 g of crotonyl chloride were added at 0° C. After the mixture had been left to stand for 24 h, it was diluted with water and washed with dilute hydrochloric acid, water and bicarbonate solution. The organic phase was evaporated to leave 2.8 g of 8-ocimenyl crotonate, which had the same isomeric composition as the starting material. In order to determine the sensory properties, the individual isomers were isolated in pure form by preparative gas chromatography.

Crotonates:

(Z3,Z6)-8-Ocimenyl crotonate: fresh, sweetish-fruity.
(E3,Z6)-8-Ocimenyl crotonate: fresh, green, galbanum.
(Z3,E6)-8-Ocimenyl crotonate: green, fatty, somewhat fresh.
(E3,E6)-8-Ocimenyl crotonate: fruity, sweetish, fatty, floral.

| Mass spectra of the 8-ocimenyl crotonates | | | | | | | |
|---|---|---|---|---|---|---|---|
| (3Z,6Z) m/z | Intens. (%) | (3E,6Z) m/z | Intens. (%) | (3Z,6E) m/z | Intens. (%) | (3E,6E) m/z | Intens. (%) |
| 69 | 100 | 119 | 100 | 69 | 100 | 69 | 100 |
| 119 | 95 | 69 | 81 | 119 | 55 | 119 | 75 |
| 41 | 40 | 134 | 38 | 41 | 30 | 134 | 32 |
| 91 | 37 | 41 | 38 | 91 | 26 | 41 | 31 |
| 134 | 34 | 91 | 34 | 134 | 23 | 91 | 28 |
| 39 | 24 | 39 | 23 | 92 | 21 | 79 | 19 |
| 92 | 24 | 79 | 19 | 39 | 17 | 39 | 18 |
| 105 | 22 | 105 | 19 | 79 | 17 | 93 | 17 |
| 79 | 20 | 92 | 17 | 93 | 17 | 105 | 16 |
| 93 | 19 | 77 | 17 | 105 | 16 | 92 | 16 |
| 220 (M+) | 0.12 | 220 (M+) | 0.12 | 220 (M+) | 0.22 | 220 (M+) | 0.15 | e) 8-Ocimenyl isobutyrate:

3.2 g of the crude product obtained under 3a and 2.5 g of pyridine were dissolved in 25 ml of diethyl ether, and 2.7 g of isobutyryl chloride were added at 0° C. After the rmixture had been left to stand for 24 h, it was diluted with water and washed with dilute hydrochloric acid, water and bicarbonate solution. The organic phase was evaporated to leave 4.6 g of 8-ocimenyl isobutyrate, which had the same isomeric composition as the starting material. In order to determine the sensory properties, the individual isomers were isolated in pure form by preparative gas chromatography.

Isobutyrates:

(Z3,Z6)-8-Ocimenyl isobutyrate: fatty, fruity, green.
(E3,Z6)-8-Ocimenyl isobutyrate: green, galbanum, fatty, fruity.
(Z3,E6)-8-Ocimenyl isobutyrate: fresh, fruity, ester-like.
(E3,E6)-8-Ocimenyl isobutyrate: slightly fresh, floral.

Mass spectra of the 8-ocimenyl isobutyrates

| (3Z,6Z) m/z | Intens. (%) | (3E,6Z) m/z | Intens. (%) | (3Z,6E) m/z | Intens. (%) | (3E,6E) m/z | Intens. (%) |
|---|---|---|---|---|---|---|---|
| 119 | 100 | 119 | 100 | 43 | 100 | 119 | 100 |
| 43 | 61 | 43 | 50 | 119 | 98 | 43 | 77 |
| 91 | 33 | 134 | 33 | 71 | 47 | 134 | 36 |
| 134 | 31 | 91 | 29 | 92 | 42 | 71 | 33 |
| 41 | 26 | 41 | 23 | 91 | 41 | 91 | 33 |
| 92 | 24 | 105 | 17 | 134 | 37 | 41 | 28 |
| 71 | 22 | 79 | 17 | 93 | 36 | 79 | 25 |
| 105 | 21 | 92 | 17 | 41 | 35 | 93 | 24 |
| 93 | 20 | 71 | 16 | 105 | 29 | 92 | 23 |
| 79 | 20 | 93 | 16 | 79 | 29 | 105 | 21 |
| 222 ($M^+$) | 0.09 | 222 ($M^+$) | 0.06 | 222 ($M^+$) | 0.21 | 222 ($M^+$) | <0.01 | f) 8-Ocimenyl butyrate:

3.2 g of the crude product obtained under 3a and 2.5 g of pyridine were dissolved in 25 ml of diethyl ether, and 2.7 g of butyryl chloride were added at 0° C. After the mixture had been left to stand for 24 h, it was diluted with water and washed with dilute hydrochloric acid, water and bicarbonate solution. The organic phase was evaporated to leave 4.6 g of 8-ocimenyl butyrate, which had the same isomeric composition as the starting material. In order to determine the sensory properties, the individual isomers were isolated in pure form by preparative gas chromatography.

Butyrates:

(Z3,Z6)-8-Ocimenyl butyrate: fresh, green, fruity.
(E3,Z6)-8-Ocimenyl butyrate: green, fruity, galbanum, pineapple.
(Z3,E6)-8-Ocimenyl butyrat: slightly green, fresh, fruity.
(E3,E6)-8-Ocimenyl butyrate: slightly fatty, fresh, fruity.

Mass spectra of the 8-ocimenyl butyrates

| (3Z,6Z) m/z | Intens. (%) | (3E,6Z) m/z | Intens. (%) | (3Z,6E) m/z | Intens. (%) | (3E,6E) m/z | Intens. (%) |
|---|---|---|---|---|---|---|---|
| 119 | 100 | 119 | 100 | 119 | 100 | 119 | 100 |
| 43 | 45 | 43 | 37 | 43 | 72 | 43 | 57 |
| 91 | 33 | 134 | 34 | 71 | 69 | 71 | 49 |
| 71 | 33 | 91 | 28 | 92 | 45 | 134 | 36 |
| 134 | 31 | 41 | 23 | 91 | 42 | 91 | 32 |
| 41 | 26 | 71 | 22 | 93 | 37 | 41 | 28. |
| 92 | 24 | 105 | 17 | 134 | 37 | 79 | 25 |
| 105 | 20 | 92 | 16 | 41 | 34 | 93 | 24 |
| 93 | 20 | 79 | 16 | 105 | 30 | 92 | 22 |
| 79 | 19 | 93 | 15 | 79 | 29 | 105 | 21 |
| 222 ($M^+$) | 0.13 | 222 ($M^+$) | 0.12 | 222 ($M^+$) | 0.34 | 222 ($M^+$) | 0.17 |

Example 4

Preparation of a perfume having a pronounced floral note:

The following components were mixed (all data in g):

| | | |
|---|---|---|
| Aldehyde C11 | 10% in isopropyl myristate | 5 |
| Aldehyde C10 | 10% in benzyl alcohol | 5 |
| Aldehyde C11 MOA | 10% in benzyl alcohol | 3 |
| Citronellyl oxyacetaldehyde | 50% in diethyl phthalate | 2 |
| Farenal ® H&R | | 3 |
| Tridecenal | 10% in diethyl phthalate | 5 |
| Hexenol tr.-2- | 10% in benzyl alcohol | 2 |
| VERTOCITRAL ® H&R | | 1 |
| Linalyl acetate | | 45 |
| CITYIAL ® H&R | | 5 |
| Citral | | 5 |
| Orange oil bitter | | 5 |
| MANDARINAL ® (Firmenich) | | 4 |
| LILIAL ® (Givaudan) | | 75 |
| LYRAL ® (IFF) | | 75 |
| Nerolidol | | 5 |
| PROFARNESOL ® H&R | | 5 |
| Linalool | | 45 |
| Phenyl ethyl alcohol | | 75 |
| Geraniol | | 10 |
| Nerol | | 10 |
| Geranium oil, African | | 5 |
| Hexyl cinamaldehyde | | 50 |
| Methyl dihydrojasmonate | | 15 |
| Benzyl salicylate | | 100 |
| Nonadienol, tr.-2-,cis-6- | 0.1% in isopropyl myristate | 5 |
| Allyl ionone | | 3 |
| ISORALDEIN ® (Givaudan) | 70 | 75 |
| Eugenol | | 7 |
| Cedryl acetate | | 40 |
| Vetiveryl acetate | | 10 |
| SANDOLEN ® (H&R) | | 5 |
| GALAXOLIDE ® (IFF) | 50% in benzyl benzoate | 50 |
| Isopropyl myristate | | 245 |
| Total | | 1000 |

By replacing 2 g of isopropyl myristate with 2 g of an ocimenyl acetate isomeric mixture containing 30–50% of (E3,Z6)-8-ocimenyl acetate, the perfume composition became fresher and more radiant, a significant potency and diffusion-enhancing effect being notable. Value and luxuriousness of the perfume composition were increased considerably as a result of (E3,Z6)-8-ocimenyl acetate being added.

Example 5

Preparation of a fruit flavour

The following components were mixed (all data in g):

| | | |
|---|---|---|
| Aldehyde C14, so-called | | 0.5 |
| Allyl capronate | | 11 |
| Caproic acid | | 4 |
| Citronellol | | 0.3 |
| Lemon oil | | 2 |
| Ethyl butyrate | | 18 |
| Ethyl capronate | | 2 |
| Ethyl heptanoate | | 1 |
| Ethyl pelargonate | | 0.5 |
| FURANEOL ® (Firmenich) | 15% in 1,2-propylene glycol, | 50 |
| Isoamyl butyrate | | 0.5 |
| Methyl 3-methylthio-propionate | | 1.3 |
| Propionic acid | | 4.5 |
| Propylene glycol, 1,2- | | 904.4 |
| Total | | 1000 |

If 10 g of propylene glycol were replaced by 10 g of a 1 percent solution (in triacetin) of an ocimenyl acetate isomeric mixture having a content of 30–50% of (E3,Z6)-8-ocimenyl acetate, the aroma became considerably more fruity and more reminiscent of pineapple; the flavor impression was enhanced overall.

What is claimed is:

1. A compound of formula (I):

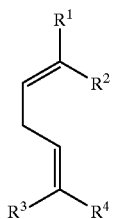

wherein one of $R^1$ and $R^2$ is methyl and the other is vinyl, and
one of $R^3$ and $R^4$ is methyl and the other is

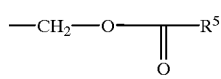

wherein $R^5$ is hydrogen, $C_1$–$C_6$ alkyl, or $C_2$–$C_6$ alkenyl.

2. The compound of claim 1 wherein $R^5$ is methyl, ethyl, n-propyl, isopropyl, n-butyl, sec-butyl, isobutyl, tert-butyl, or 2-butenyl.

3. The compound of claim 1, which is:

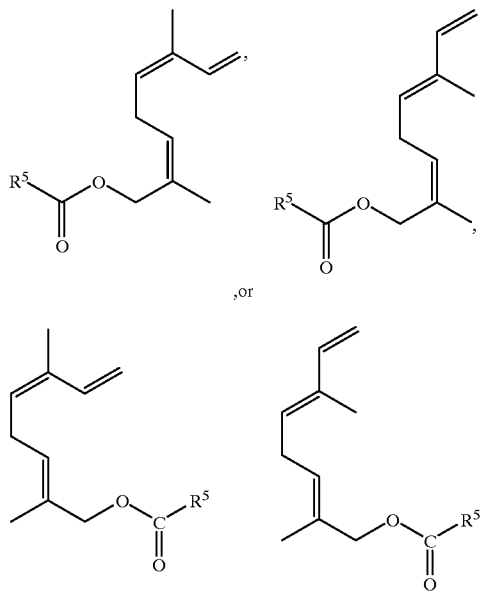

wherein $R^5$ is hydrogen, $C_1$–$C_6$ alkyl, or $C_2$–$C_6$ alkenyl.

4. A process for preparing the compound of formula (I)

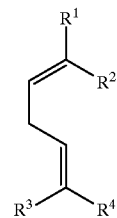

wherein
one of $R^1$ and $R^2$ is methyl and the other is vinyl, and
one of $R^3$ and $R^4$ is methyl and the other is
wherein $R^5$ is hydrogen, $C_1$–$C_6$ alkyl, or $C_2$–$C_6$ alkenyl, comprising reacting a compound of formula (II)

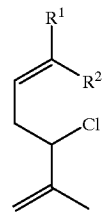

wherein one of $R^1$ and $R^2$ is methyl and the other is vinyl with an alkali metal salt of an aliphatic $C_2$–$C_7$ carboxylic acid.

5. The process of claim 4 wherein the alkali metal salt is a Na- or a K-salt.

6. The process of claim 4 wherein the alkali metal salt is sodium acetate.

7. The process of claim 4 carried out in a solvent selected from the group consisting of dimethylformamide, dimethyl sulphoxide, N-methylpyrrolidone, and diethyl glycol dimethyl ether, and mixtures thereof.

8. The process of claim 4 carried out in the presence of an alkali metal iodide.

9. The process of claim 8 wherein the alkali metal iodide is NaI.

10. The process of claim 9 wherein NaI is present in an amount from 0.01% to 10% by weight, the weight being based on 100 parts of the weight of the compound of formula (II).

11. A composition comprising a carrier and a compound of formula (I)

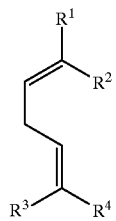

wherein one of $R^1$ and $R^2$ is methyl and the other is vinyl, and one of $R^3$ and $R^4$ is methyl and the other is

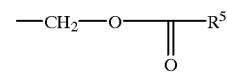

wherein $R^5$ is hydrogen, $C_1$–$C_6$ alkyl, or $C_2$–$C_6$ alkenyl, and wherein the carrier is a fragrance, a flavor, or a perfume oil.

* * * * *